(12) United States Patent  
Shirai et al.

(10) Patent No.: US 11,945,773 B2
(45) Date of Patent: Apr. 2, 2024

(54) METHOD FOR PRODUCING PROPIONIC ACID DERIVATIVE

(71) Applicant: DAIKIN INDUSTRIES, LTD., Osaka (JP)

(72) Inventors: Atsushi Shirai, Osaka (JP); Asako Yoshiyama, Osaka (JP); Makoto Matsuura, Osaka (JP); Yoshichika Kuroki, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 2 days.

(21) Appl. No.: 17/698,252

(22) Filed: Mar. 18, 2022

(65) Prior Publication Data

US 2022/0259132 A1   Aug. 18, 2022

Related U.S. Application Data

(63) Continuation of application No. PCT/JP2020/036909, filed on Sep. 29, 2020.

(30) Foreign Application Priority Data

Sep. 30, 2019  (JP) .................................. 2019-179617
Jan. 6, 2020   (JP) .................................. 2020-000399

(51) Int. Cl.
  *C07C 51/31*   (2006.01)
  *B01D 39/06*   (2006.01)
  *C07C 51/47*   (2006.01)

(52) U.S. Cl.
  CPC .............. *C07C 51/31* (2013.01); *B01D 39/06* (2013.01); *C07C 51/47* (2013.01); *B01D 2239/1241* (2013.01); *B01D 2239/125* (2013.01)

(58) Field of Classification Search
  CPC ......... C07C 51/31; C07C 51/47; C07C 51/58; C07C 59/315; C07C 67/26; B01D 39/06
  See application file for complete search history.

(56) References Cited

U.S. PATENT DOCUMENTS 4,719,052 A * 1/1988 Ohsaka ................... C07C 51/58
                                                         560/145
2009/0176942 A1  7/2009 Ishikawa et al.

FOREIGN PATENT DOCUMENTS

JP     61-130254        6/1986
JP     H0617338 B2 *    3/1994  ........... H01L 21/304
(Continued)

OTHER PUBLICATIONS

JP H0617338, Aisaka Yonosuke, et al., Novel Fluorine-containing polyester ester, English translation, 3 pages (Year: 1994).*
(Continued)

*Primary Examiner* — Yate' K Cutliff
(74) *Attorney, Agent, or Firm* — Wenderoth, Lind & Ponack, L.L.P.

(57) ABSTRACT

An object of the present invention is to provide a method for producing a propionic acid derivative with high productivity. The object can be achieved by a method for producing a compound represented by formula (1):

(Continued)

wherein $R^1$ is a halogen atom or the like, $R^2$ and $R^3$ are each independently a hydrogen atom, a halogen atom, or an organic group, X is an oxygen atom or a sulfur atom, $R^4$ and $R^5$ are each independently a hydrogen atom, a halogen atom, or a hydrocarbon group optionally having one or more substituents, $R^6$ is a hydrocarbon group optionally having one or more substituents; the method comprising step A of reacting a compound represented by formula (2):

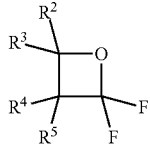

(2)

with a compound represented by formula (3):
$M(R^1)_n$, wherein M is a cation, n is an integer corresponding to the valence of M, and a compound represented by formula (4):
$R^6$—X—H; and
step B of separating, by filtration, the compound represented by formula (5): $MF_n$ from the mixture obtained by the above reaction.

18 Claims, 2 Drawing Sheets

(56) References Cited

FOREIGN PATENT DOCUMENTS

| WO | WO-199003409 A1 * | 4/1990 | ............ C08G 65/00 |
| WO | WO-2010071108 A1 * | 6/2010 | ............ C07C 31/38 |

OTHER PUBLICATIONS

WO 2010071108, Yamashita, T. et al., Fluoroalcohol and fluoromonomer, English Translation, 22 pages (Year: 2010).*
Yamada, S. et al., Easy access to CF2-containing molecules base on the reaction of 2,2,3,3-tetrafluorooxetane with various nucleophiles, Organic & biomolecular chemistry, vol. 9, No. 15, pp. 5493-5502 (Year: 2011).*
Yamada, S. et al., Easy access to CF2-containing molecules base on the reaction of 2,2,3,3-tetrafluorooxetane with various nucleophiles, Organic & biomolecular chemistry, vol. 9, No. 15, Supplementary Information. 61 pages, (pp. 18-23) (Year: 2011).*
Shigeyuki Yamada et al., "Easy access to $CF_2$-containing molecules based on the reaction of 2,2,3,3-tetrafluorooxetane with various nucleophiles", Organic & Biomolecular Chemistry, 2011, vol. 9, No. 15, pp. 5493-5592.
International Preliminary Report on Patentability dated Apr. 5, 2022 in International (PCT) Application No. PCT/JP2020/036909.
Extended European Search Report dated Oct. 16, 2023 in corresponding European Patent Application No. 20871963.3.

* cited by examiner

METHOD FOR PRODUCING PROPIONIC ACID DERIVATIVE

TECHNICAL FIELD

The present disclosure relates to a method for producing a propionic acid derivative.

BACKGROUND ART

Propionic acid derivatives, such as 2,2-difluoropropionic acid esters, are useful compounds as raw materials of pharmaceuticals, agricultural chemicals, etc. As a method for producing 2,2-difluoropropionic acid esters, a method for reacting 2,2,3,3-tetrafluorooxetane with alcohols or phenols in the presence of an alkali metal halide is known (Patent Literature 1).

CITATION LIST

Patent Literature

PTL 1: JP1986-130254A

SUMMARY

The present disclosure includes the following embodiments.

A method for producing a compound represented by formula (1):

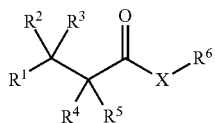

(1)

wherein $R^1$ is a halogen atom or SR, wherein R is a hydrogen atom or a hydrocarbon group, $R^2$ and $R^3$ are each independently a hydrogen atom, a halogen atom, or an organic group, or $R^2$ and $R^3$ optionally form a ring together with a carbon atom at the β-position, X is an oxygen atom or a sulfur atom, $R^4$ and $R^5$ are each independently a hydrogen atom, a halogen atom, or a hydrocarbon group optionally having one or more substituents, or $R^4$ and $R^5$ optionally form a ring together with a carbon atom at the α position, $R^6$ is a hydrocarbon group optionally having one or more substituents;

the method comprising step A of reacting a compound represented by formula (2):

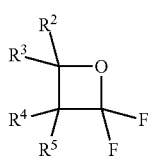

(2)

wherein $R^2$ to $R^5$ are as defined above, with a compound represented by formula (3):

$$M(R^1)_n \tag{3}$$

wherein

M is a cation, n is an integer corresponding to the valence of M, and $R^1$ is as defined above, and a compound represented by formula (4):

$$R^6—X—H \tag{4}$$

wherein $R^6$ and X are as defined above; and step B of separating, by filtration, the compound represented by formula (5):

$$MF_n \tag{5}$$

wherein

M and n are as defined above, from the mixture obtained by the above reaction.

Advantageous Effects

According to the present disclosure, a method for producing a propionic acid derivative having high productivity is provided.

DESCRIPTION OF EMBODIMENTS

Figure 1:
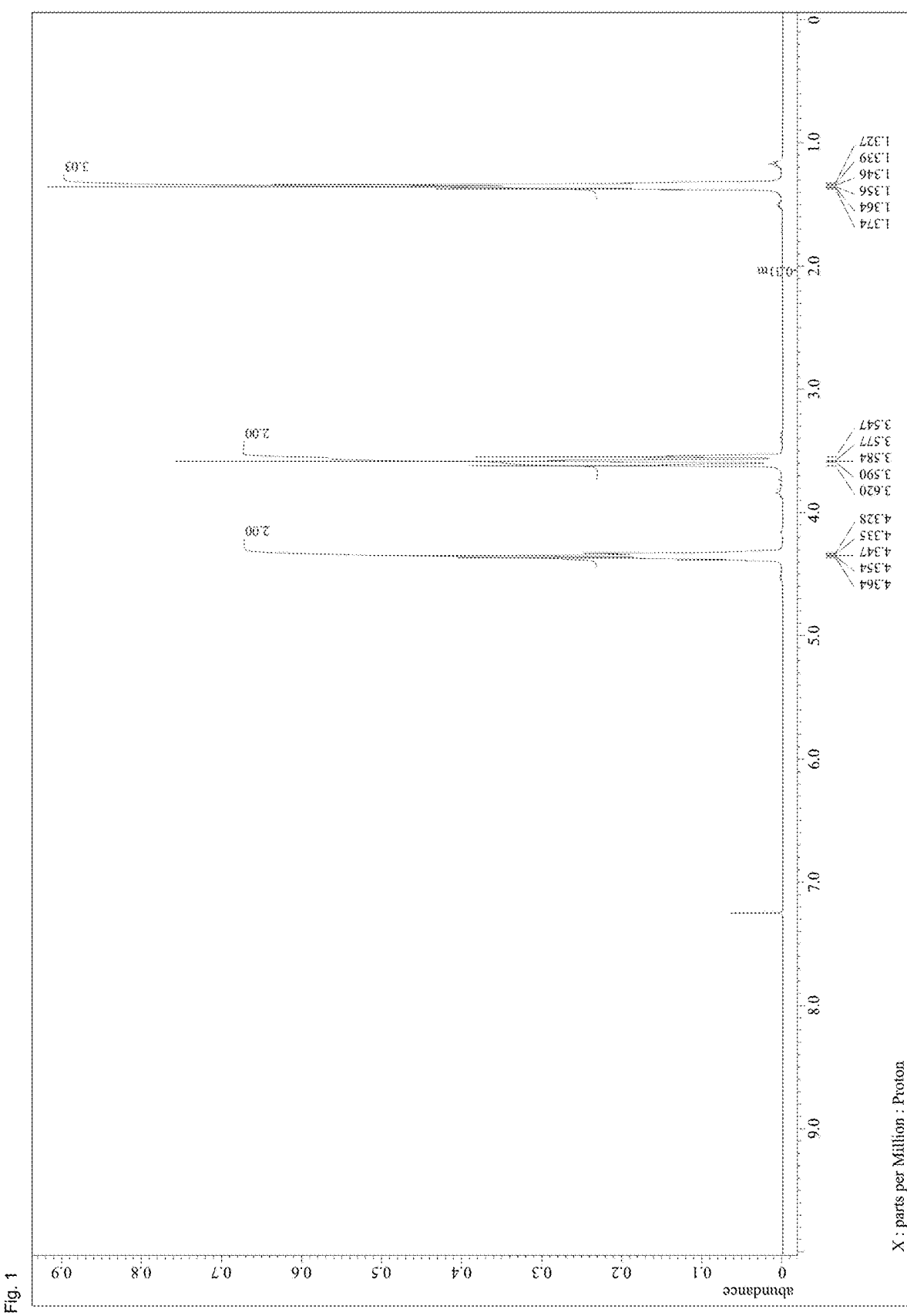
FIG. 1 is a diagram showing the $^1$H-NMR spectrum of $ICH_2CF_2COOEt$.

The above summary of the present disclosure is not intended to describe each disclosed embodiment or every implementation of the present disclosure.

The description of the present disclosure that follows more specifically exemplifies illustrative embodiments.

In several places throughout the present disclosure, guidance is provided through lists of examples, and these examples can be used in various combinations.

In each instance, the described list serves only as a representative group, and should not be interpreted as an exclusive list.

All of the publications, patents, and patent applications cited herein are incorporated herein by reference in their entirety.

1. Term

The symbols and abbreviations in the present specification can be understood in the sense commonly used in the technical field to which the present disclosure pertains in the context of the present specification, unless otherwise specified.

In the present specification, the terms "comprise" and "contain" are used with the intention of including the phrases consisting essentially of and consisting of.

Unless otherwise specified, the steps, treatments, and operations described in the present specification can be performed at room temperature.

In the present specification, "room temperature" means a temperature within the range of 10 to 40° C.

In the present specification, the phrase "$C_{n-m}$" (n and m each represent a number) indicates that the number of carbon atoms is n or more and m or less, as can typically be understood by a person skilled in the art.

Unless otherwise specified, examples of the "halogen atom" as referred to in the present specification include fluorine, chlorine, bromine, and iodine.

The "organic group" as referred to in the present specification means a group formed by removing one hydrogen atom from an organic compound.

Examples of the "organic group" as referred to in the present specification include hydrocarbon groups optionally having one or more substituents, non-aromatic heterocyclic groups optionally having one or more substituents, heteroaryl groups optionally having one or more substituents, a cyano group, an aldehyde group, QO-, QS-, QCO-, $QSO_2$-, QOCO-, and $QOSO_2$-, wherein Q is independently a hydrocarbon group optionally having one or more substituents, a non-aromatic heterocyclic group optionally having one or more substituents, or a heteroaryl group optionally having one or more substituents.

Examples of the "substituents" include halogen atoms, a cyano group, an amino group, alkoxy groups, and alkylthio groups. Two or more substituents may be identical to or different from each other. The number of substituents can be selected from the range of 1 to the maximum substitutable number, and it may be 1, 2, 3, or 4.

Unless otherwise specified, examples of "hydrocarbon groups" as referred to in the present specification include alkyl, alkenyl, alkynyl, cycloalkyl, cycloalkenyl, cycloalkadienyl, aryl, and aralkyl.

Unless otherwise specified, examples of the "alkyl" as referred to in the present specification include linear or branched $C_{1-20}$ alkyl groups, such as methyl, ethyl, propyl (n-propyl, isopropyl), butyl (n-butyl, isobutyl, sec-butyl, tert-butyl), pentyl, and hexyl.

Unless otherwise specified, the "haloalkyl" as referred to in the present specification is an alkyl group optionally substituted with one or more halogen atoms. Examples of the haloalkyl group include fluoromethyl, difluoromethyl, trifluoromethyl (perfluoromethyl), 2-fluoroethyl, 2,2-difluoroethyl, 2,2,2-trifluoroethyl, 1,1,2,2-tetrafluoroethyl, pentafluoroethyl (perfluoroethyl), and linear or branched-chain halo $C_{1-20}$ alkyl groups, such as groups in which some or all of the fluorine atoms are replaced by other halogen atoms.

Unless otherwise specified, examples of the "alkoxy" as referred to in the present specification include linear or branched $C_{1-20}$ alkoxy groups, such as methoxy, ethoxy, propoxy (n-propoxy and isopropoxy), butoxy (n-butoxy, isobutoxy, sec-butoxy, and tert-butoxy), pentyloxy, and hexyloxy.

Unless otherwise specified, examples of the "alkylthio" as referred to in the present specification include linear or branched $C_{1-20}$ alkylthio groups, such as methylthio, ethylthio, propylthio (n-propylthio and isopropylthio), butylthio (n-butylthio, isobutylthio, sec-butylthio, and tert-butylthio), pentylthio, and hexylthio.

Unless otherwise specified, examples of the "alkenyl" as referred to in the present specification include linear or branched $C_{2-20}$ alkenyl groups, such as vinyl, 1-propen-1-yl, 2-propen-1-yl, isopropenyl, 2-buten-1-yl, 4-penten-1-yl, and 5-hexen-1-yl.

Unless otherwise specified, examples of the "alkynyl" as referred to in the present specification include linear or branched $C_{2-20}$ alkynyl groups, such as ethynyl, 1-propyn-1-yl, 2-propin-1-yl, 4-pentyn-1-yl, and 5-hexyn-1-yl.

Unless otherwise specified, examples of the "cycloalkyl" as referred to in the present specification include $C_{3-10}$ cycloalkyl groups, such as cyclopropyl, cyclobutyl, cyclopentyl, cyclohexyl, and cycloheptyl.

Unless otherwise specified, examples of the "cycloalkenyl" as referred to in the present specification include $C_{3-10}$ cycloalkenyl groups, such as cyclopropenyl, cyclobutenyl, cyclopentenyl, cyclohexenyl, and cycloheptenyl.

Unless otherwise specified, examples of the "cycloalkadienyl" as referred to in the present specification include $C_{4-10}$ cycloalkadienyl groups, such as cyclobutadienyl, cyclopentadienyl, cyclohexadienyl, cycloheptadienyl, cyclooctadienyl, cyclononadienyl, and cyclodecadienyl.

Unless otherwise specified, the "aryl" as referred to in the present specification can be monocyclic, bicyclic, tricyclic, or tetracyclic.

Unless otherwise specified, the "aryl" as referred to in the present specification can be a $C_{6-18}$ aryl group.

Unless otherwise specified, examples of the "aryl" as referred to in the present specification include phenyl, 1-naphthyl, 2-naphthyl, 2-biphenyl, 3-biphenyl, 4-biphenyl, and 2-anthryl.

Unless otherwise specified, the "haloaryl" as referred to in the present specification is an aryl group optionally substituted with one or more halogen atoms.

Unless otherwise specified, examples of the "aralkyl" as referred to in the present specification include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylmethyl, 3-biphenylmethyl, and 4-biphenylmethyl. Unless otherwise specified, the "haloaralkyl" as referred to in the present specification is an aralkyl group optionally substituted with one or more halogen atoms.

Unless otherwise specified, the "non-aromatic heterocyclic group" as referred to in the present specification means a group formed by removing one hydrogen atom from a non-aromatic heterocycle.

Unless otherwise specified, the "non-aromatic heterocyclic group" as referred to in the present specification can be monocyclic, bicyclic, tricyclic, or tetracyclic.

Unless otherwise specified, the "non-aromatic heterocyclic group" as referred to in the present specification can be saturated or unsaturated.

Unless otherwise specified, the "non-aromatic heterocyclic group" as referred to in the present specification can be a 5- to 18-membered non-aromatic heterocyclic group.

Unless otherwise specified, the "non-aromatic heterocyclic group" as referred to in the present specification can be, for example, a non-aromatic heterocyclic group containing, in addition to carbon atoms, 1 to 4 heteroatoms selected from oxygen, sulfur, and nitrogen atoms as a ring-constituting atom.

Unless otherwise specified, examples of the "non-aromatic heterocyclic group" as referred to in the present specification include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydrofuran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, and the like.

Unless otherwise specified, the "heteroaryl" as referred to in the present specification can be monocyclic, bicyclic, tricyclic, or tetracyclic.

Unless otherwise specified, the "heteroaryl" as referred to in the present specification can be, for example, a 5- to 18-membered heteroaryl group.

Unless otherwise specified, the "heteroaryl" as referred to in the present specification can be, for example, a heteroaryl group containing, in addition to carbon atoms, 1 to 4 heteroatoms selected from oxygen, sulfur, and nitrogen atoms as a ring-constituting atom.

Unless otherwise specified, examples of the "heteroaryl" as referred to in the present specification include "monocyclic heteroaryl groups" and "aromatic fused heterocyclic groups."

Unless otherwise specified, examples of the "monocyclic heteroaryl groups" as referred to in the present specification include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-3-yl and 1,2,4-triazol-4-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), pyrazinyl, and the like.

Unless otherwise specified, examples of the "aromatic fused heterocyclic groups" as referred to in the present specification include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl), and the like.

Production Method of Compound Represented by Formula (1)

In one embodiment, the method for producing a compound represented by formula (1):

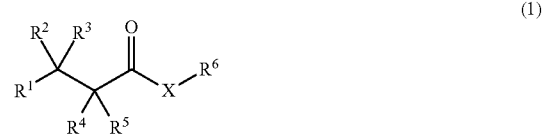

(1)

wherein $R^1$ is a halogen atom or SR, wherein R is a hydrogen atom or a hydrocarbon group, $R^2$ and $R^3$ are each independently a hydrogen atom, a halogen atom, or an organic group, or $R^2$ and $R^3$ optionally form a ring together with a carbon atom at the β-position, X is an oxygen atom or a sulfur atom, $R^4$ and $R^5$ are each independently a hydrogen atom, a halogen atom, or a hydrocarbon group optionally having one or more substituents, or $R^4$ and $R^5$ optionally form a ring together with a carbon atom at the α position, $R^6$ is a hydrocarbon group optionally having one or more substituents, the method including step A of reacting a compound represented by formula (2):

(2)

wherein $R^2$ to $R^5$ are as defined above, with a compound represented by formula (3):

$$M(R^1)_n \qquad (3),$$

wherein

M is a cation, n is an integer corresponding to the valence of M, and $R^1$ is as defined above, and a compound represented by formula (4):

$$R^6-X-H \qquad (4),$$

wherein $R^6$ and X are as defined above; and step B of separating, by filtration, the compound represented by formula (5):

$$MF_n \qquad (5),$$

wherein

M and n are as defined above, from the mixture obtained by the above reaction.

Compound Represented by Formula (1)

$R^1$ is preferably a halogen atom, a mercapto group, or an alkylthio group; more preferably a halogen atom; even more preferably a fluorine atom, a chlorine atom, a bromine atom, or an iodine atom; still more preferably a bromine atom or an iodine atom; and particularly preferably an iodine atom.

It is preferable that $R^2$ and $R^3$ are each independently a hydrogen atom, a halogen atom, an alkyl group, or a haloalkyl group; more preferably a hydrogen atom, a halogen atom, a $C_{1-4}$ alkyl group, or a halo $C_{1-4}$ alkyl group; even more preferably a hydrogen atom or a halogen atom; still more preferably a hydrogen atom or a fluorine atom; and particularly preferably a hydrogen atom.

The ring formed by $R^2$ and $R^3$ together with the carbon atom at the β-position is not limited, and can be, for example, a 5- to 8-membered aliphatic or heterocyclic ring (e.g., a nitrogen-containing heterocyclic ring, an oxygen-containing heterocyclic ring, or a sulfur-containing heterocyclic ring) optionally having one or more substituents.

It is preferable that $R^4$ and $R^5$ are each independently a hydrogen atom, a halogen atom, an alkyl group, or a haloalkyl group; more preferably a hydrogen atom, a halogen atom, a $C_{1-4}$ alkyl group, or a halo $C_{1-4}$ alkyl group; even more preferably a halogen atom; and particularly preferably a fluorine atom.

The ring formed by $R^4$ and $R^5$ together with the carbon atom at the α-position is not particularly limited, and can be, for example, a 5- to 8-membered aliphatic or heterocyclic ring (e.g., a nitrogen-containing heterocyclic ring, an oxygen-containing heterocyclic ring, and a sulfur-containing heterocyclic ring) optionally having one or more substituents.

$R^6$ is preferably an alkyl group optionally having one or more substituents, an aryl group optionally having one or more substituents, or an aralkyl group optionally having one or more substituents; more preferably an alkyl group, a haloalkyl group, an aryl group, a haloaryl group, an aralkyl group, or a haloaralkyl group; even more preferably an alkyl group or a haloalkyl group; and particularly preferably a $C_{1-6}$ alkyl group or a halo $C_{1-6}$ alkyl group.

X is preferably an oxygen atom.

Step A $R^2$ to $R^5$ in formula (2) can be individually a group corresponding to $R^2$ to $R^5$ in formula (1). Examples of the compound represented by formula (2) include 2,2-difluorooxetanes, and typically 2,2,3,3-tetrafluorooxetane. The compounds represented by formula (2) may be used alone or in a combination of two or more.

$R^1$ in formula (3) can be a group corresponding to $R^1$ in formula (1). The cation represented by M in formula (3) is not particularly limited as long as it is a counter ion of $R^1$, and examples include hydrogen, metal, ammonium, and the like. Examples of the metal include alkali metals and alkaline earth metals. Examples of the alkali metals include lithium, sodium, potassium, and cesium. Examples of the alkaline earth metals include magnesium and calcium. Specific examples of the ammonium include primary to quaternary ammonium. Examples of the primary ammonium include $C_{1-6}$ alkylamines such as methylamine, ethylamine, propylamine (n-propylamine, isopropylamine), and butylamine, and aniline.

Examples of the secondary ammonium include di-C1-6 alkylamines such as dimethylamine, diethylamine, ethylmethylamine, and dipropylamine, pyrrolidine, imidazole, piperidine, and morpholine.

Examples of the tertiary ammonium include tri-$C_{1-6}$ alkylamines such as trimethylamine and triethylamine, pyridine, and quinoline.

Examples of the quaternary ammonium include tetra-$C_{1-6}$ alkylammonium such as tetramethylammonium and tetraethylammonium. M is preferably a metal, more preferably an alkali metal or an alkaline earth metal, and even more preferably an alkali metal.

n can be suitably selected according to the valence of M, and is, for example, 1 or 2.

Examples of the compound represented by formula (3) include NaI, KI, CsI, $MgI_2$, $CaI_2$, NaBr, KBr, CsBr, $MgBr_2$, $CaBr_2$, NaCl, KCl, CsCl, $MgCl_2$, and $CaCl_2$.

The compounds represented by formula (3) can be used alone or in a combination of two or more.

The lower limit of the amount of the compound represented by formula (3) can be, for example, 0.1 mole, preferably 0.5 mole, and even more preferably 0.9 mole, relative to 1 mole of the compound represented by formula (2).

The upper limit of the amount of the compound represented by formula (3) can be, for example, 10 moles, preferably 5 moles, and even more preferably 3 moles, relative to 1 mole of the compound represented by formula (2).

The amount of the compound represented by formula (3) can be, for example, 0.1 to 10 moles, preferably from 0.5 to 5 moles, and even more preferably 0.9 to 3 moles, relative to 1 mole of the compound represented by formula (2).

$R^6$ and X in formula (4) can be respectively groups corresponding to $R^6$ and X in formula (1).

Specific examples of the compound represented by formula (4) include alcohols, phenols, and thiols. Examples of the alcohols include $C_{1-6}$ alkanols such as methanol, ethanol, propanol (n-propanol and isopropanol), and butanol. Examples of the phenols include phenol, cresol, and naphthol. Examples of the mercaptans (thiols) include $C_{1-6}$ alkyl mercaptans such as methyl mercaptan, ethyl mercaptan, propyl mercaptan (n-propyl mercaptan and isopropyl mercaptan), and butyl mercaptan.

The compound represented by formula (4) may be used alone or in a combination of two or more.

The lower limit of the amount of the compound represented by formula (4) can be, for example, 0.1 moles, preferably 0.5 moles, and even more preferably 0.9 moles, relative to 1 mole of the compound represented by formula (2).

The upper limit of the amount of the compound represented by formula (4) can be, for example, 10 moles, preferably 5 moles, and even more preferably 3 moles, relative to 1 mole of the compound represented by formula (2).

The amount of the compound represented by formula (4) can be, for example, 0.1 to 10 moles, preferably 0.5 to 5 moles, and even more preferably 0.9 to 3 moles, relative to 1 mole of the compound represented by formula (2).

In the reaction of step A, the compound represented by formula (4) may be used as a solvent, or a component other than the compound represented by formula (4) may be used as a solvent. When the compound represented by formula (4) is used as a solvent, it can be preferably 10 moles or more relative to 1 mole of the compound represented by formula (2).

Examples of the component other than the compound represented by formula (4) include aliphatic hydrocarbons (e.g., hexane), aromatic hydrocarbons (e.g., toluene, xylene), halogenated hydrocarbons (e.g., dichloromethane, dichloroethane, and chloroform), ethers (e.g., diethyl ether and tetrahydrofuran), ketones (e.g., acetone, methyl ethyl ketone), nitriles (e.g., acetonitrile), esters (e.g., ethyl acetate), amides (e.g., dimethylformamide (DMF) and dimethylacetamide (DMAc)).

The components other than the compound represented by formula (4) may be used alone or in a combination of two or more.

In the reaction of step A, the reaction temperature and the reaction time are not particularly limited as long as the reaction proceeds.

The lower limit of the reaction temperature can be, for example, −70° C., preferably −20° C., and even more preferably 0° C.

The upper limit of the reaction temperature can be, for example, 150° C., preferably 100° C., and even more preferably 80° C.

The reaction temperature can be, for example, in the range of −70 to 150° C., preferably −20 to 100° C., even more preferably 0 to 80° C.

The lower limit of the reaction time can be, for example, 0.5 hours, preferably 1 hour, and even more preferably 1.5 hours.

The upper limit of the reaction time can be, for example, 12 hours, preferably 10 hours, and even more preferably 5 hours.

The reaction time is in the range of, for example, 0.5 to 12 hours, preferably 1 to 10 hours, and even more preferably 1.5 to 5 hours.

Step B

Step B is capable of highly removing the compound represented by formula (5) from the reaction mixture obtained in step A.

M and n in formula (5) can respectively correspond to M and n in formula (3). Examples of the compound represented by formula (5) include NaF, KF, CsF, $CaF_2$, and the like.

The compound represented by formula (5) can be a compound with low solubility in water and/or an organic solvent. The solubility at 20° C. can be, for example, 100 g/L or less, preferably 80 g/L or less, and even more preferably 50 g/L or less.

The method of filtration is not limited. The filtration can usually be performed using a filter material, and preferably using a filter material and a filter aid. The method using a filter material and a filter aid may be pre-coating (a method of filtration using a product in which a filter aid layer is formed on a filter material), or body feeding (a method of filtration by adding a filter aid to the reaction mixture in step A).

Examples of the filter material include paper, metal (e.g., stainless steel), polymer (e.g., cellulose, polypropylene, polyester, and polyamide), glass, ceramics, cloth, etc.

The filter material is preferably porous, for example, a porous membrane or a porous filter.

The average pore diameter of the filter material is not limited, and is, for example, 0.01 to 20 μm, preferably 0.01 to 15 μm, and even more preferably 0.01 to 10 μm.

Examples of the filter aid include diatomite (e.g., Celite (trademark)), filter sand (e.g., manganese sand, manganese zeolite, activated carbon, anthracite, ceramic sand), perlite, and cellulose. The filter aids can be used alone or in a combination of two or more. The filter aid is preferably diatomite.

The filter aid, for example, has an average particle size of 0.5 to 200 μm, preferably 1 to 150 μm, and even more preferably 1 to 100 μm.

The filtration temperature (internal temperature of the reaction mixture subjected to filtration) is not particularly limited. In terms of filtration efficiency, filtration is preferably performed at room temperature or more.

The lower limit of the filtration temperature is preferably 45° C., more preferably 50° C., 55° C., 60° C., or 65° C.

The upper limit of the filtration temperature is preferably 90° C., more preferably 85° C., and even more preferably 80° C.

The filtration temperature is preferably 45° C. or more, and more preferably in the range of 45 to 90° C.

The filtration can be performed under atmospheric pressure, under pressure, or under reduced pressure, for example, at −2 to 2 MPa, and preferably at −1 to 1 MPa.

Step C

It is preferable that the method for producing the compound represented by formula (1) further includes step C of performing a liquid separation treatment on the filtrate obtained by the filtration. By combining the steps B and C, the compound represented by formula (5) can be further removed.

The liquid separation treatment usually includes the step of adding water and an organic solvent to the filtrate, the step of separating the mixture into the aqueous phase and the organic phase, and collecting the organic phase.

Examples of the organic solvent used in the liquid separation treatment include aliphatic hydrocarbons (e.g., hexane), aromatic hydrocarbons (e.g., toluene and xylene), halogenated hydrocarbons (e.g., dichloromethane, and dichloroethane), ethers (e.g., diethyl ether and tetrahydrofuran), ketones (e.g., methyl ethyl ketone), esters (e.g., ethyl acetate), and the like.

The organic solvents may be used alone or in a combination of two or more. The organic solvent is preferably an ether.

The method for producing the compound represented by formula (1) may further include another optional step. Examples of such a step include distillation, concentration, washing, or a combination of two or more steps.

Composition Comprising Compound Represented by Formula (1) and Compound Represented by Formula (5)

In one embodiment, the composition is a composition comprising a compound represented by formula (1) and a compound represented by formula (5), wherein the fluorine ion content concentration is more than 0 mg/L and 1000 mg/L or less.

The upper limit of the fluorine ion content concentration can be preferably 900 mg/L, 800 mg/L, 700 mg/L, 600 mg/L, 500 mg/L, 400 mg/L, 300 mg/L, 200 mg/L, or 150 mg/L.

The lower limit of the fluorine ion content concentration can be usually the detection limit or 0.001 mg/L.

The fluorine ion content concentration can be, for example, in the range of 0.001 to 1000 mg/L.

The composition further contains the compound represented by formula (4).

The lower limit of the content of the compound represented by formula (4) in the composition can be, for example, the detection limit or 0.01 mass %.

The upper limit of the content of the compound represented by formula (4) in the composition may be, for example, 5 mass %, and preferably 3 mass %.

The content of the compound represented by formula (4) in the composition can be, for example, 5 mass % or less, or in the range of 0.01 to 5 mass %.

The present disclosure includes the following embodiments.

Item 1. A method for producing a compound represented by formula (1):

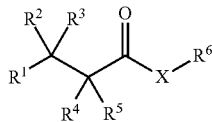 (1)

wherein
R$^1$ is a halogen atom or SR, wherein R is a hydrogen atom or a hydrocarbon group,
R$^2$ and R$^3$ are each independently a hydrogen atom, a halogen atom, or an organic group, or R$^2$ and R$^3$ optionally form a ring together with a carbon atom at the β-position,
X is an oxygen atom or a sulfur atom,
R$^4$ and R$^5$ are each independently a hydrogen atom, a halogen atom, or a hydrocarbon group optionally having one or more substituents, or R$^4$ and R$^5$ optionally form a ring together with a carbon atom at the α position,
R$^6$ is a hydrocarbon group optionally having one or more substituents;
the method comprising
step A of reacting a compound represented by formula (2):

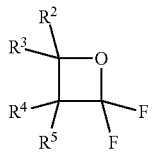 (2)

wherein
R$^2$ to R$^5$, are as defined above, with a compound represented by formula (3):

M(R$^1$)$_n$ (3), wherein
M is a cation, n is an integer corresponding to the valence of M, and R$^1$ is as defined above, and a compound represented by formula (4):

R$^6$—X—H (4), wherein
R$^6$ and X are as defined above; and step B of separating, by filtration, the compound represented by formula (5):

MF$_n$ (5), wherein
M and n are as defined above,
from the mixture obtained by the above reaction.

Item 2. The production method according to Item 1, wherein the filtration is performed at a temperature of 45° C. or more.

Item 3. The production method according to Item 1 or 2, wherein the filtration is performed using a filter material and a filter aid.

Item 4. The production method according to Item 3, wherein the filter aid is at least one member selected from the group consisting of diatomaceous earth, filter sand, perlite, and cellulose.

Item 5. The production method according to Item 3 or 4, wherein the average particle size of the filter aid is in the range of 0.5 to 200 μm.

Item 6. The production method according to any one of Items 1 to 5, further comprising step C of performing a liquid separation treatment on a filtrate obtained by the filtration.

Item 7. The production method according to any one of Items 1 to 6, wherein R$^1$ is a chlorine atom, a bromine atom, or an iodine atom.

Item 8. The production method according to any one of Items 1 to 7, wherein R$^1$ is a bromine atom or an iodine atom.

Item 9. The production method according to any one of Items 1 to 8, wherein R$^2$ and R$^3$ are each independently a hydrogen atom, a halogen atom, an alkyl group, or a haloalkyl group.

Item 10. The production method according to any one of Items 1 to 9, wherein R$^2$ and R$^3$ are hydrogen atoms.

Item 11. The production method according to any one of Items 1 to 10, wherein R$^4$ and R$^5$ are each independently a hydrogen atom, a halogen atom, an alkyl group, or a haloalkyl group.

Item 12. The production method according to any one of Items 1 to 11, wherein R$^4$ and R$^5$ are halogen atoms.

Item 13. The production method according to any one of Items 1 to 12, wherein R$^4$ and R$^5$ are fluorine atoms.

Item 14. The production method according to any one of Items 1 to 13, wherein R$^6$ is an alkyl group or a haloalkyl group.

Item 15. The production method according to any one of Items 1 to 14, wherein R$^6$ is a C$_{1-6}$ alkyl group or a halo C$_{1-6}$ alkyl group.

Item 16. The production method according to any one of Items 1 to 15, wherein X is an oxygen atom.

Item 17. The production method according to any one of Items 1 to 16, wherein M is a metal.

Item 18. The production method according to any one of Items 1 to 17, wherein M is an alkali metal or an alkaline earth metal.

Item 19. The production method according to any one of Items 1 to 18, wherein M is an alkali metal.

Item 20. A composition comprising a compound represented by formula (1):

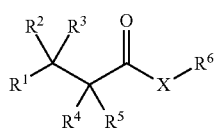 (1)

wherein
R$^1$ is a halogen atom or SR, wherein R is a hydrogen atom or a hydrocarbon group,
R$^2$ and R$^3$ are each independently a hydrogen atom, a halogen atom, or an organic group, or R$^2$ and R$^3$ optionally form a ring together with a carbon atom at the β-position,
X is an oxygen atom or a sulfur atom,
R$^4$ and R$^5$ are each independently a hydrogen atom, a halogen atom, or a hydrocarbon group optionally having one or more substituents, or
R$^4$ and R$^5$ optionally form a ring together with a carbon atom at the α position,
R$^6$ is a hydrocarbon group optionally having one or more substituents; and a compound represented by formula (5):

MF$_n$ (5), wherein

M is an alkali metal, and n is an integer corresponding to the valence of M;

the composition having a fluorine ion content concentration of more than 0 mg/L and 1000 mg/L or less.

Item 21. The composition according to Item 20, wherein $R^1$ is a chlorine atom, a bromine atom, or an iodine atom.

Item 22. The composition according to Item 20 or 21, wherein $R^1$ is a bromine atom or an iodine atom.

Item 23. The composition according to any one of Items 20 to 22, wherein $R^2$ and $R^3$ are each independently a hydrogen atom, a halogen atom, an alkyl group, or a haloalkyl group.

Item 24. The composition according to any one of Items 20 to 23, wherein $R^2$ and $R^3$ are hydrogen atoms.

Item 25. The composition according to any one of Items 20 to 24, wherein $R^4$ and $R^5$ are each independently a hydrogen atom, a halogen atom, an alkyl group, or a haloalkyl group.

Item 26. The composition according to any one of Items 20 to 25, wherein $R^4$ and $R^5$ are halogen atoms.

Item 27. The composition according to any one of Items 20 to 26, wherein $R^4$ and $R^5$ are fluorine atoms.

Item 28. The composition according to any one of Items 20 to 27, wherein $R^6$ is an alkyl group or a haloalkyl group.

Item 29. The composition according to any one of Items 20 to 28, wherein $R^6$ is a $C_{1-6}$ alkyl group or a halo $C_{1-6}$ alkyl group.

Item 30. The composition according to any one of Items 20 to 29, wherein X is an oxygen atom.

Item 31. The composition according to any one of Items 20 to 30, wherein M is a metal.

Item 32. The composition according to any one of Items 20 to 31, wherein M is an alkali metal or an alkaline earth metal.

Item 33. The composition according to any one of Items 20 to 32, wherein M is an alkali metal.

The present disclosure also includes ethyl 2,2-difluoro-3-iodo-propionate ($ICH_2CF_2COOEt$).

EXAMPLES

One embodiment of the present disclosure is described in more detail by means of the Examples; however, the present disclosure is not limited to these.

Example 1

A solution of tetrafluorooxetane (75 wt % chloroform solution, 80 g, 0.462 mol) in ethanol (18.8 g) was added dropwise over 1 hour to a suspension of sodium iodide (69.3 g, 0.462 mol) in ethanol (60 g) under ice cooling. After dropwise addition, the temperature was raised to 50° C., and the mixture was stirred under heating for 2 hours. The resulting reaction mixture (internal temperature: 50° C.) was filtered using a filter material (paper product, average pore diameter: 4.0 μm) and a filter aid (Celite (trademark), average particle size: 12 to 20 μm), and ethanol was distilled off to obtain $ICH_2CF_2COOEt$ (yield: 90.8%).

Figure 2:
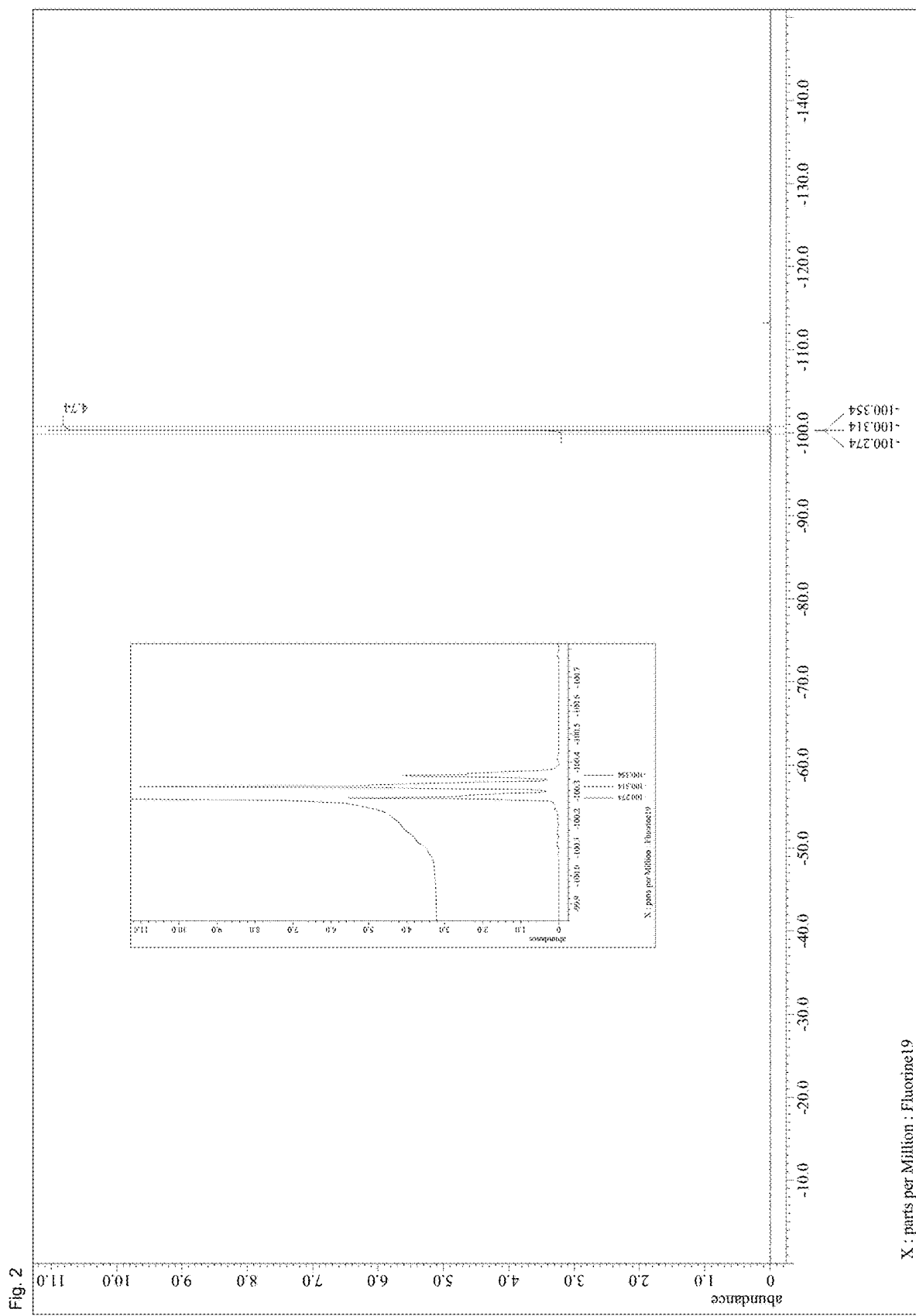
FIG. 2 is a diagram showing the $^{19}$F-NMR spectrum of $ICH_2CF_2COOEt$.

FIGS. 1 and 2 show the $^1H$-NMR spectrum and $^{19}F$-NMR spectrum of $ICH_2CF_2COOEt$, respectively.

Comparative Example 1

$ICH_2CF_2COOEt$ was obtained by the same operation as in Example 1, except that a liquid separation treatment was performed by the addition of water and diethyl ether to the reaction mixture in place of filtration.

Example 2

$ICH_2CF_2COOEt$ was obtained by the same operation as in Example 1 except that after filtration, water and diethyl ether were added to a filtrate to perform a liquid separation treatment.

The F ion content concentration in the products of Example 1, Comparative Example 1, and Example 2 was measured by the following method.

1. 1 g of a sample was weighed in a plastic container.

2. 1 g of KOH was weighed in a plastic container, and distilled water was added thereto to make 100 g of a KOH aqueous solution.

3. 5 g of the 1% KOH aqueous solution prepared in Item 2 was added to the plastic container of Item 1.

4. The lid of the plastic container of Item 3 was closed, followed by mixing, and the container was allowed to stand. The supernatant was introduced into a disposable syringe with a filter (pore diameter: 0.45 μm), followed by filtration.

5. 1 g of the filtrate obtained in Item 4 was taken out, and 5 mL of distilled water was added thereto, followed by stirring. Thereafter, 4 mL of the upper layer was taken out and transferred into another centrifuge tube. 4 mL of TISAB (total ionic strength adjustment buffer) (produced by Merck Sharp and Dohme) was added thereto, followed by stirring and measurement with an F ion meter.

The following table shows the measurement results of the F ion concentration.

TABLE 1

| | F ion concentration contained in 1 g of sample (mg/L) |
|---|---|
| Example 1 | 104 |
| Comparative Example 1 | 1104 |
| Example 2 | 21 |

Example 3

$ICH_2CF_2COOMe$ (yield: 81.5%) was obtained by the same operation as in Example 1 except that the ethanol used in Example 1 was changed to methanol.

Example 4

$BrCH_2CF_2COOEt$ (yield: 61.1%) was obtained by the same operation as in Example 1 except that the sodium iodide used in Example 1 was changed to sodium bromide.

Examples 5 to 8

One hundred grams of the reaction mixture obtained in Example 1 was filtered under the conditions shown in Table 2. The time required for the filtration was as shown in Table 2.

TABLE 2

| | Filtration temperature (inner temperature of a reaction mixture) (° C.) | Filtration pressure | Filter material [1] | Filter aid [2] | Time required for filtration |
|---|---|---|---|---|---|
| Example 5 | 65 | Ordinal pressure | Used | Used | 9 min. 39 sec. |
| Example 6 | 25 | Ordinal pressure | Used | Used | 13 min. 45 sec. |
| Example 7 | 65 | Ordinal pressure | Used | Not used | 4 min. 3 sec. |
| Example 8 | 25 | Ordinal pressure | Used | Not used | 12 min. 9 sec. |

[1] Paper product, average pore diameter: 4.0 μm
[2] Celite (trademark), average particle diameter: 12 to 20 μm

The invention claimed is:

1. A method for producing a compound represented by formula (1):

wherein
- $R^1$ is a chlorine atom, a bromine atom, an iodine atom, or SR, wherein R is a hydrogen atom or a hydrocarbon group,
- $R^2$ and $R^3$ are hydrogen atoms,
- X is an oxygen atom,
- $R^4$ and $R^5$ are fluorine atoms,
- $R^6$ is a $C_{1-6}$ alkyl group, a haloalkyl group, or an aryl group;

the method comprising
step A of reacting a compound represented by formula (2):

wherein
$R^2$ to $R^5$ are as defined above, with a compound represented by formula (3):

$$M(R^1)_n \qquad (3),$$

wherein
M is cation, n is an integer corresponding to the valence of M, and $R^1$ is as defined above, and a compound represented by formula (4):

$$R^6-X-H \qquad (4),$$

wherein
$R^6$ and X are as defined above;
step B of separating, by filtration, a compound represented by formula (5):

$$MF_n \qquad (5),$$

wherein
M and n are as defined above,
from the a mixture obtained by the above reaction; and
step C of performing a liquid separation treatment on a filtrate obtained by the filtration.

2. The production method according to claim 1, wherein the filtration is performed at a temperature of 45° C. or more.

3. The production method according to claim 1, wherein the filtration is performed using a filter material and a filter aid.

4. The production method according to claim 3, wherein the filter aid is at least one member selected from the group consisting of diatomite, filter sand, perlite, and cellulose.

5. The production method according to claim 3, wherein the average particle size of the filter aid is in the range of 0.5 to 200 μm.

6. The production method according to claim 1, wherein $R^1$ is a bromine atom or an iodine atom.

7. The production method according to claim 1, wherein $R^6$ is a $C_{1-6}$ alkyl group or a haloalkyl group.

8. The production method according to claim 1, wherein $R^6$ is a $C_{1-6}$ alkyl group or a halo $C_{1-6}$ alkyl group.

9. The production method according to claim 1, wherein M is a metal.

10. The production method according to claim 1, wherein M is an alkali metal or an alkaline earth metal.

11. The production method according to claim 1, wherein M is an alkali metal.

12. A composition comprising a compound represented by formula (1):

wherein
- $R^1$ is a chlorine atom, a bromine atom, an iodine atom, or SR, wherein R is a hydrogen atom or a hydrocarbon group,
- $R^2$ and $R^3$ are hydrogen atoms,
- X is an oxygen atom,
- $R^4$ and $R^5$ are fluorine atoms,
- $R^6$ is a $C_{1-6}$ alkyl group, a haloalkyl group, or an aryl group; and a compound represented by formula (5):

$$MF_n \qquad (5),$$

wherein
M is a cation, and n is an integer corresponding to the valence of M;
the composition having a fluorine ion content concentration of more than 0 mg/L and 1000 mg/L or less.

13. The composition according to claim 12, wherein $R^1$ is a bromine atom or an iodine atom.

14. The composition according to claim 12, wherein $R^6$ is a $C_{1-6}$ alkyl group or a haloalkyl group.

15. The composition according to claim 12, wherein $R^6$ is a $C_{1-6}$ alkyl group or a halo $C_{1-6}$ alkyl group.

16. The composition according to claim 12, wherein M is a metal.

17. The composition according to claim 12, wherein M is an alkali metal or an alkaline earth metal.

18. The composition according to claim 12, wherein M is an alkali metal.

* * * * *